| United States Patent [19] | [11] | 4,093,646 |
|---|---|---|
| Bamfield et al. | [45] | June 6, 1978 |

[54] REDUCTION OF NITRO COMPOUNDS WITH AQUEOUS SOLUTIONS OF A FORMATE

[75] Inventors: Peter Bamfield; Peter Michael Quan; Trevor James Smith, all of Manchester, England

[73] Assignee: Imperial Chemical Industries Limited, London, England

[21] Appl. No.: 599,345

[22] Filed: Jul. 28, 1975

[30] Foreign Application Priority Data

Aug. 19, 1974  United Kingdom ............... 36361/74

[51] Int. Cl.$^2$ ................. C07C 143/56; C07C 143/64; C07C 101/72
[52] U.S. Cl. .................................. 260/508; 260/509; 260/510; 260/518 R; 260/519; 548/371; 548/372; 548/373; 548/374; 560/19

[58] Field of Search ........... 260/508, 509, 510, 507 R, 260/518 R, 471 A, 310 A, 310 C, 580, 519

[56] References Cited

U.S. PATENT DOCUMENTS

| 2,276,587 | 3/1942 | Mettler et al. ....................... 260/508 |
| 3,293,295 | 12/1966 | Swakon et al. ...................... 260/580 |

OTHER PUBLICATIONS

Yoneyama, Derwent Abstract, JA-4742713-Q (1972).
Yoneyama, Derwent Abstract, JA-4861402-Q (1973).

*Primary Examiner*—Nicky Chan
*Attorney, Agent, or Firm*—Cushman, Darby & Cushman

[57] ABSTRACT

A process for the reduction of organic nitro compounds containing groups which confer solubility in water comprising treatment of said compounds with an aqueous solution of a formate in presence of a hydrogenation catalyst.

10 Claims, No Drawings

REDUCTION OF NITRO COMPOUNDS WITH AQUEOUS SOLUTIONS OF A FORMATE

This invention relates to a process for the reduction in aqueous solution of organic nitro compounds containing solubilising groups.

It is known that organic nitro compounds containing water solubilising groups such as sulphonic, carboxylic groups, phenolic groups or amino groups may be reduced for example by treatment with metallic iron and hydrochloric acid in aqueous medium, or with hydrogen gas in presence of a hydrogenation catalyst. However, such processes require specialised equipment and are not always convenient to operate.

According to the present invention we provide a process for the reduction of organic nitro compounds containing groups which confer solubility in water comprising treatment of said compounds with an aqueous solution of a formate in presence of a hydrogenation catalyst.

The formate used in the process may be formic acid or a water-soluble salt thereof, or a mixture of such salts, or of such salts and free formic acid. As formic acid salts there may be used for example alkali metal formates, and especially sodium formate. Preferably strong solutions of formate are used, for example of at least 10% strength by weight.

For complete reduction of each nitro group to an amino group at least three molar proportions of formate should be present.

As hydrogenation catalysts there may be used for example those based on platinum, palladium and ruthenium, and especially palladium supported on 5 to 100 times its weight of carbon. To give a useful reaction rate there may be used for example between 0.1 and 15 parts of palladium-on-carbon catalyst per 100 parts of organic nitro compound. After reaction the catalyst may be collected and re-used.

To increase the reaction rate, especially at lower catalyst usages, it has been found useful in some cases to treat the solution of organic nitro compound with activated carbon before the addition of the catalyst. As has been found with catalytic hydrogenation reactions it may also be advantageous to add catalytic amounts of other metal compounds and especially ferric hydroxide.

The pH at which the reduction process is conducted preferably lies between 2 and 12, and most conveniently between 3 and 10; pH adjustment may be effected if necessary using formic acid or mineral acids or the commonly used alkaline substances such as sodium hydroxide and sodium carbonate.

Although the reaction may proceed at lower temperatures it is usually found convenient to conduct the reduction process at the boil in an atmosphere of an inert gas such as nitrogen.

The process of the present invention is especially useful for reducing to the corresponding amino compounds aromatic nitro compounds of the benzene and naphthalene series which contain sulphonic acid or carboxylic acid solubilising groups.

The invention is illustrated but not limited by the following examples in which parts are by weight.

EXAMPLE 1

To a solution of 25.9 parts of the disodium salt of a 1-nitronaphthalene-3,6-8-trisulphonic acid in 125 parts of water are added 20.4 parts of sodium formate and 1.5 parts of damp 3% palladium on carbon catalyst (0.93 parts dry weight). The mixture is covered with a nitrogen atmosphere and stirred and heated under reflux for 26 hours. The mixture is then cooled and the catalyst is collected by filtration. Analysis of the filtrate by ultra violet spectroscopy and by titration of an aliquot with sodium nitrite solution shows it to contain 22.2 parts of 1-aminonaphthalene-3,6,8-trisulphonic acid (98% of the theoretical yield).

EXAMPLE 2

A solution of 20.6 parts of the magnesium salt of 3-nitronaphthalene-1,5-disulphonic acid and 5.5 parts of sulphuric acid in 160 parts of water is reacted with 20.4 parts of sodium formate and 1.24 parts (dry weight) of 3% palladium-on-carbon catalyst according to the procedure of Example 1. After 22 hours a further 10 parts of sodium formate are added and stirring under reflux is continued for an additional period of 20 hours. The mixture is cooled and filtered and the filter cake is washed with dilute sulphuric acid until only the catalyst remains on the filter. Analysis of the combined filtrates by ultraviolet spectroscopy and by titration of an aliquot with sodium nitrite solution indicates that the theoretical yield (17.6 parts) of 3-aminonaphthalene-1,5-disulphonic acid has been formed.

EXAMPLE 3

A mixture of 27.6 parts of 3-acetylamino-4-hydroxy-5-nitrobenzene sulphonic acid, 75 parts of sodium formate, and 6 parts of damp 3% palladium on charcoal (3 parts dry weight) catalyst in 300 parts of water is stirred together at room temperature for 10 minutes and is then raised to the boil during 30 minutes. The solution is boiled under reflux during 4 hours until the orange solution becomes clear pale brown and no nitro group can be detected and then the catalyst is filtered off. The filtrates are acidified to Congo Red test papers with concentrated hydrochloric acid and then a further 20 parts of concentrated hydrochloric acid are added followed by 10% w/v of sodium chloride. The suspension is stirred at room temperature for several hours to complete the precipitation and then 3-acetylamino-5-amino-4-hydroxybenzenesulphonic acid (22 parts) is filtered off, washed with small amounts of 10% w/v sodium chloride solution, and dried.

EXAMPLES 4 – 30 (Table I)

Example 2 is repeated, replacing the 20.6 parts of the magnesium salt of 3-nitronaphthalene-1,5-disulphonic acid by the equivalent number of parts (based on nitro group content) of the nitro compounds listed in Table I. The pH of the mixture is adjusted by addition of sodium hydroxide or sulphuric acid to achieve solubility of the starting material. The corresponding amino compounds are produced in excellent yields and if desired may be isolated from solution by procedures well known to the art.

Table I

| Ex. | Organic Nitro compound |
| --- | --- |
| 4 | 1-nitronaphthalene-5-sulphonic acid |
| 5 | 1-nitronaphthalene-6-sulphonic acid |
| 6 | 1-nitronaphthalene-7-sulphonic acid |
| 7 | 1-nitronaphthalene-8-sulphonic acid |
| 8 | 1,4-dinitrobenzene-2-sulphonic acid |
| 9 | 4-nitroacetanilide-3-sulphonic acid |
| 10 | 2,4-dinitromesitylene-6-sulphonic acid |
| 11 | 2-nitrotoluene-4-sulphonic acid |
| 12 | 5-nitro-2-methoxy-N-$\beta(\beta'$-methoxyethoxycarbonyl)-ethylaniline |

Table I-continued

| Ex. | Organic Nitro compound |
|---|---|
| 13 | 5-acetylamino-2-nitrobenzoic acid |
| 14 | 1-carboxy-2-hydroxy-3-nitrobenzene-5-sulphonic acid |
| 15 | 2-nitrophenol-4-sulphonic acid |
| 16 | 2-nitrobenzene sulphonic acid |
| 17 | 3-nitrobenzene sulphonic acid |
| 18 | 1-nitronaphthalene-3,8-disulphonic acid |
| 19 | 1-nitronaphthalene-4,8-disulphonic acid |
| 20 | 1-nitronaphthalene-4,6,8-trisulphonic acid |
| 21 | 4-nitro-4'-aminodiphenylamine-2-sulphonic acid |
| 22 | N-cyclohexyl-4-nitroaniline-2-sulphonic acid |
| 23 | 4-nitro-2'-methoxydiphenylamine-2-sulphonic acid |
| 24 | 6-nitroindazole |
| 25 | 1-(3'-nitro-2'-methyl-5'-sulphophenyl)-3-carboxy-5-pyrazolone |
| 26 | 1-nitroanthraquinone-5-sulphonic acid |
| 27 | 1-nitroantraquinone-8-sulphonic acid |
| 28 | 4,4'-dinitrostilbene-2,2'-disulphonic acid |
| 29 | 2-methoxy-5-nitrobenzene sulphonic acid |
| 30 | 4-methoxy-3-nitrobenzene sulphonic acid |

We claim:

1. In a process for the reduction of aromatic nitro compounds selected from the class consisting of nitronaphthalene monosulphonic acids, nitronaphthalene disulphonic acids, nitronaphthalene trisulphonic acids, nitrobenzene sulphonic acids, dinitrobenzene sulphonic acids, dinitromesitylene sulphonic acid, substituted nitrobenzene sulphonic acids in which the substituents are selected from acetylamino, methyl, methoxy, hydroxy, aminoanilino, methoxyanilino, cyclohexylamino and β-(nitro-sulphophenyl)-ethenyl, and substituted nitrobenzene carboxylic acids in which the substituents are selected from acetylamino, hydroxy and sulphonic acid, the improvement which consists of treatment of said compounds with an aqueous solution of a formate in the presence of a hydrogenation catalyst based on platinum, palladium or ruthenium at a temperature up to the boiling point and at a pH of 2 to 12.

2. A process according to claim 1 wherein the formate is sodium formate.

3. A process according to claim 1 wherein the aqueous solution of formate is of at least 10% strength by weight.

4. A process according to claim 1 wherein at least three molar equivalents of formate are present for each nitro group, whereby to reduce each nitro group to an amino group.

5. A process according to claim 1 wherein the hydrogenation catalyst comprises palladium supported on 5 to 100 times its weight of carbon.

6. A process according to claim 5 wherein from 0.1 to 15 parts by weight of the palladium-on-carbon catalyst are used for each 100 parts by weight of organic nitro compound.

7. A process according to claim 1 wherein an aqueous solution of the organic nitro compound is treated with activated carbon before addition of the hydrogenation catalyst.

8. A process according to claim 1 wherein ferric hydroxide is present to increase the activity of the hydrogenation catalyst.

9. A process according to claim 1 carried out at a pH of 3 to 10.

10. A process according to claim 1 conducted at or near the boiling point.

* * * * *